United States Patent [19]

Kimler et al.

[11] Patent Number: 5,393,731
[45] Date of Patent: Feb. 28, 1995

[54] WATER DISPERSIBLE GRANULAR HERBICIDAL COMPOSITIONS COMPRISING DINITROANILINE AND IMIDAZOLINONE HERBICIDES WITH MONTMORILLONITE CARRIERS

[75] Inventors: Joseph Kimler, Yardville; Robert Kubisch, Martinsville, both of N.J.

[73] Assignee: American Cyanamid Company, Wayne, N.J.

[21] Appl. No.: 164,169

[22] Filed: Dec. 8, 1993

Related U.S. Application Data

[63] Continuation-in-part of Ser. No. 996,412, Dec. 23, 1992, Pat. No. 5,296,450, and Ser. No. 996,221, Dec. 23, 1992, Pat. No. 5,294,594.

[51] Int. Cl.$^6$ .................. A01N 25/08; A01N 25/14; A01N 33/18; A01N 43/50
[52] U.S. Cl. ................... 504/139; 71/DIG. 1
[58] Field of Search ................... 504/116, 139

[56] References Cited

U.S. PATENT DOCUMENTS

| | | | |
|---|---|---|---|
| 4,007,258 | 2/1977 | Cohen et al. | 424/22 |
| 4,162,154 | 7/1979 | Gates et al. | 71/88 |
| 4,511,395 | 4/1985 | Misselbrook | 71/121 |
| 4,657,582 | 4/1987 | Huber | 71/121 |
| 5,019,155 | 5/1991 | Kimpara et al. | 71/121 |
| 5,180,420 | 1/1993 | Katayama et al. | |
| 5,290,754 | 3/1994 | Nishii et al. | 504/232 |

FOREIGN PATENT DOCUMENTS 0112438 4/1984 European Pat. Off. .

OTHER PUBLICATIONS

Chemical Patents Index, Basic Abstracts Journal, Section Ch, Week 8637, 5 Nov. 1986, CA-A-1 209 363 (BASF Wyandotte Corp) 12 Aug. 1986.
Chemical Patents Index, Documentation Abstracts Journal, Section Ch, Week 8915, 7 Jun. 1989, JP-A-1 056 602 (Shionogi KK) 3 Mar. 1989.

*Primary Examiner*—Richard L. Raymond
*Assistant Examiner*—S. Mark Clardy
*Attorney, Agent, or Firm*—Michael P. Morris

[57] ABSTRACT

The present invention relates to water dispersible granular compositions comprising a dinitroaniline herbicide and an imidazolinone herbicide with a montmorillonite carrier, and to a process for the preparation of the compositions. Such compositions are storage stable and possess desirable dispersion properties.

20 Claims, No Drawings

WATER DISPERSIBLE GRANULAR HERBICIDAL COMPOSITIONS COMPRISING DINITROANILINE AND IMIDAZOLINONE HERBICIDES WITH MONTMORILLONITE CARRIERS

This is a continuation-in-part of application Ser. No. 07/996,412, filed on Dec. 23, 1992, now U.S. Pat. No. 5,296,450, and Ser. No. 07/996,221, filed on Dec. 23, 1992, now U.S. Pat. No. 5,294,594.

BACKGROUND OF THE INVENTION

Water dispersible granules (WDG's) are becoming increasingly important in the formulation of agricultural compositions because they are more safely handled and environmentally friendly than other commonly used formulations. For example, chemical spills of WDG's are easily cleaned, no toxic solvents are present in the WDG formulation, and it is possible to package WDG's in water soluble packaging, thus reducing user exposure.

The typical processes for making WDG's are pan granulation, spray drying, fluid bed granulation, and mixing agglomeration. The choice of which process to use depends on several factors, including the physical and chemical properties of the active ingredient(s), environmental and safety aspects, and volume and packaging requirements.

Pan granulation typically produces compositions having good dispersibility and can be used for low-melt, active ingredients. The disadvantage of pan granulation is that the granules are often dusty, and the size distribution of the granule is difficult to control. Spray drying typically produces compositions in high volume and with good dispersibility, however, the bulk density of the product is usually low and it is difficult to spray dry low-melt, active ingredients. Fluid bed granulation has basically the same advantages/disadvantages as spray drying, while mixing agglomeration has similar advantages/disadvantages as pan granulation.

Dinitroaniline herbicides, which are useful for the selective control of certain grasses and broadleaf weeds, have typically been formulated as emulsifiable concentrates, flowables, wettable powders or the like, which are diluted in a tank mix. These formulations, however, require handling, measuring and mixing prior to application to the soil.

Conventional dispersible granular compositions containing dinitroaniline herbicides have been difficult to prepare. Such herbicides, which are solid at room temperature but have melting points below 100° C., have a tendency to cake, fuse or lump up when stored at or exposed to elevated temperatures, due to the excessive softening or partial melting of the herbicides. Moreover, they are often dusty and may cause staining.

The imidazolinone class of herbicides, such as imazaquin, imazethapyr, imazamethapyr and imazamethabenz-methyl, are highly desirable for the selective control of a wide variety of grass and broadleaf weeds in the presence of agricultural crops at exceptionally low rates of application. At present, imidazolinone herbicides are commercially available mainly in the form of liquid compositions. However, as environmental concerns increase, there is an ever-growing need for an effective granular composition containing an imidazolinone herbicide. The prior art's pan granulated compositions present the common drawbacks of dusting, variable particle size distribution, and lack of ease of water dispersibility.

Efforts to produce stable granular formulations comprising such dinitroaniline herbicides, alone, or in combination with imidazolinone herbicides, without the drawbacks discussed above, and capable of uniform distribution in a solvent-free, WDG formulation, however, continue.

It is therefore an object of this invention to provide a solvent-free, water dispersible granular composition with improved dispersion properties.

It is also an object of this invention to provide a water dispersible granular composition comprising a novel dispersion enhancing agent.

It is another object of this invention to produce a non-dusting, non-staining, water dispersible granular herbicidal composition having granules of substantially uniform size and density.

It is yet another object of this invention to provide storage stable water dispersible granular herbicidal compositions comprising one or more active ingredients.

It is further object of this invention to provide a novel method for producing water dispersible granular herbicidal compositions.

These and other objects of this invention will become more evident in the detailed description that follows.

SUMMARY OF THE INVENTION

The present invention relates to water dispersible granular compositions comprising a dinitroaniline herbicide, alone, or in combination with an imidazolinone herbicide, and a dispersion enhancing agent, and to a process for the preparation of said compositions. Such compositions are storage stable and contain desirable dispersion properties.

DETAILED DESCRIPTION OF THE INVENTION

This invention provides a novel formulation of useful dinitroaniline herbicides, alone, or in combination with imidazolinone herbicides, as water dispersible granular compositions (WDG's), which offer ease of handling coupled with reduced dusting, and other environmentally desirable characteristics.

A primary concern when formulating WDG's is that the granules disperse in an acceptable amount of time. Of the conventional carriers typically considered, bentonite was among the least desirable with which to formulate a WDG because the granules are difficult to disperse. However, it has now been found that extruding the WDG with a dispersion enhancing agent permits the use of bentonite because of its compatibility with low-melt, active ingredients, such as dinitroaniline compounds. Advantageously, the use of bentonite minimizes the loss of the physical performance attributes of low-melt, active ingredients, such as dinitroanilines, compared to most other typical carriers. At the same time, such a stable formulation permits the coformulation of a dinitroaniline herbicide and an imidazolinone herbicide, thereby benefiting from the desirable and complementary properties of each active ingredient.

As used herein, the term "dispersion enhancing agent" means a chemical entity that facilitates the swelling and dispersing of the bentonite or other suitable carrier component of the WDG composition of the invention. Typically, such dispersion enhancing agents are selected from bases, such as alkali metal hydroxides and amines, and water swellable polymers, including cellulosic materials.

It has now been found that extrudable granulated herbicidal compositions comprising a dinitroaniline herbicide, alone, or in combination with and an imidazolinone herbicide, and a dispersion enhancing agent, can be formulated to possess improved suspendability and dispersibility. Such a discovery takes advantage of the beneficial properties of many components while minimizing potential incompatibility.

In a preferred embodiment, the present invention relates to water-dispersible granular compositions comprising a dinitroaniline herbicide of structural formula (I)

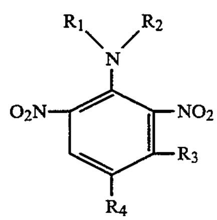

I wherein $R_1$ is selected from H, $C_1$-$C_4$ straight or branched-chain alkyl, $C_3$-$C_4$alkenyl and $C_3$-$C_4$alkynyl; $R_2$ is selected from $C_1$-$C_6$ straight or branched-chain alkyl and optionally substituted with Cl or $OCH_3$, $C_3$-$C_4$alkenyl, and $C_3$-$C_4$alkynyl; $R_3$ is H, $CH_3$ or $CH_2OCH_3$; and $R_4$ is $C_1$-$C_4$alkyl, $CF_3$ or Cl, alone, or in combination with an imidazolinone herbicide. The imidazolinone herbicide may be any of the imidazolinone compounds known in the art such as those described in U.S. Pat. Nos. 4,798,619; 4,772,311; 5,039,333; 5,108,485; and in EP 254,951 and EP 322,616. Preferably, the imidazolinone herbicide is selected from imazaquin, imazapyr, imazethapyr and imazamethapyr. A more preferred imidazolinone herbicide is imazaquin. The present invention also relates to methods of producing WDG compositions containing such compounds.

More preferred formula (I) herbicides for use in the compositions of the invention include pendimethalin (N-(1-ethylpropyl)-2,6-dinitro-3,4-xylidine) and trifluralin (N,N-dipropyl-2,6-dinitro-4-trifluoromethylaniline), as well as benfluralin, isopropalin, ethalfluralin, oryzalin (Ryzelan ®) and the like, alone, or in combination. Pendimethalin and trifluralin are most preferred.

In general, WDG's containing high concentrations of between about 20% and 90%, preferably between about 30% and 70% by weight, of low-melting dinitroanilines, such as pendimethalin and trifluralin, optionally in combination with about 1% to 20%, preferably 5% to 15% by weight of an imidazolinone herbicide, and a carrier, such as bentonite, may be prepared in a controlled manner by extrusion in the presence of a dispersion enhancing agent, such as a base or water swellable polymer, to yield essentially dust-free and uniformly granular WDG's possessing good dispersibility. Compositions containing such high concentrations of active ingredients, particularly when used in combination, provide the environmental and commercial advantage of using less material to obtain the desired result. Lower concentration pesticidal compositions, however, may also be prepared, as can compositions containing mixtures of active ingredients, depending on the needs of the particular application.

The finding that bentonite clay is suitable for preparing heat-stable, water dispersible granular compositions containing high concentrations of low melting materials is unexpected. It is contemplated that the incorporation of between about 0.5% and 20% by weight, preferably between about 1% and 10% by weight, of a base, such as sodium hydroxide, potassium hydroxide or isopropyl amine, or water-swellable polymers, for example, heterocyclic polymers such as Agrimer ® XLF (2-pyrolidinone, 1-ethenyl, homopolymer, or PVP), N-vinyl-2-pyrrolidonel(NVP), a cellulosic material, such as croscarmellose sodium (e.g., Ac-Di-Sol ®, FMC Corporation), microcrystalline cellulose (e.g., Lattice ® NTC-80), or other commercially available polyhydroxy polymers, into the WDG formulation causes the bentonite or other suitable hydrous carrier to swell upon contact with the water. Advantageously, this swelling permits the WDG to disperse more quickly.

Carriers suitable for use in the preparation of the water dispersible granular compositions of the invention include swelling clays such as kaolinate, zeolite and preferably, montmorillonite clays, such as beidellite, bentonite, nontronite and saponite. Most preferred are carriers comprising bentonite, at least in greater part, as carrier combinations may be employed. Commercially available, naturally occurring swelling clays include VOLCLAY ® (Wyoming Bentonites), VEEGUM ®, or other naturally occurring swelling clays which contain the same montmorillonite unit structure and properties.

Suitable wetting agents for use in the preparation of the WDG compositions of the invention include conventional agents such as sodium N-methyl-N-oleyoyltaurate (Igepon ® T-77), octylphenoxy polyethoxy ethanol, nonylphenoxy polyethoxy ethanol, sodium dioctyl sulfosuccinate, sodium dodecyl benzyl sulfonate, sodium lauryl sulfonate, and the like, or mixtures thereof. Suitable suspension agents include conventional agents such as sodium lignosulfonate, alkyl naphthalene sulfonates, the sodium salt of a naphthalene sulfuric acid-formaldehyde condensate (Morwet ® D-425 or Lowmar ® PW), and the like, or mixtures thereof (Morwet ® EFW). Suitable antifoaming agents include conventional detergents such as sodium tallowate (Foamaster Soap L ®) and the like. Suitable flow agents include conventional agents such as fumed silica, calcium silicate (Micro-Cel ® E), and the like, or mixtures thereof.

The WDG compositions of the invention comprise about 20 to 90% by weight (preferably 30-70%) of a dinitroaniline compound, preferably a dinitroaniline compound of formula (I), optionally about 1% to 20%, preferably 5% to 15% by weight, of an imidazolinone herbicide, preferably selected from the group consisting of imazaquin, imazethapyr, imazamethapyr and imazapyr, admixed with from about 5.0 to 25.0% by weight of one or more carriers, about 1.0-7.5% by weight of one or more wetting agents, about 2-10% by weight of one or more suspension agents, and about 0.5-20% by weight of one or more dispersion enhancing agents. More preferably, the WDG compositions of the invention also include up to about 1% by weight of one or more antifoaming agents, and up to about 7.5% by weight of one or more flow agents to facilitate the extrusion process.

The hardness, sorptivity, particle size and apparent density of the WDG composition can be adjusted by varying or combining the type(s) of clay, the type(s) of surfactants and/or wetting agents, and mixtures thereof, which are commonly employed in agricultural formulations. Other conventional formulating agents, such as disintegrating aids or thickening agents, may also be added to the WDG compositions of the invention while maintaining the desirable properties described above.

In order to prepare the WDG compositions of the invention, the appropriate dinitroaniline, and optionally imidazolinone, technical material is passed through a pin mill. The milled technical is then blended with the wetting agents, the suspension agents, and the carriers, and optionally, the anitfoaming agents and the flow agents. The blended material is milled in an air classifier mill, preferably under liquid nitrogen or other unreactive refrigerant source sufficient to cool the mill. The milled material is then mixed with water (10-15% of total batch size) and the dispersion enhancing agents, and extruded through a conventional LUWA bench top basket extruder, for example, one having about a 0.6 mm to 1.2 mm aperture. The extruded granules are allowed to dry overnight in a hood until the residual moisture is reduced to about 1-3%. The granules are then sieved through a #16 and #40 mesh screen and collected.

Many variations of this invention will occur to those skilled in the art in light of the above, detailed description. For example, combinations of water swellable polymers may be used as the dispersion enhancing agent. All such obvious variations are within the full intended scope of the appended claims.

The present invention is further illustrated by the following non-limiting examples.

EXAMPLES

Experimental Procedures

The preparation of WDG compositions of the invention for comparison testing with prior art compositions involved (a) milling about 20% to 90% by weight of a dinitroaniline herbicide, optionally with about 1% to 20% by weight of an imidazolinone herbicide; (b) blending the milled herbicide with about 1% to 7.5% by weight of one or more wetting agents, about 2% to 10% by weight of one or more suspension agents and about 5.0 to 25.0% by weight of one or more carriers; (c) milling the blend produced by step (b), preferrably in the presence of an unreactive refrigerant sufficient to cool the mill; (d) mixing about 0.5% to 20% by weight of one or more dispersion enhancing agents with water, and the milled blend produced by step (c); (e) extruding the milled blend into granular compositions; and (f) drying the extruded granular compositions.

Following the above procedures, the following WDG compositions were prepared and tested. The important physical properties of the WDG compositions of Examples 1-7 (dinitroanaline herbicides alone) and Examples 8-14 (dinitroanaline herbicides in combination with imidazolinone herbicides) are set forth in Examples 15-16.

| Ingredient | (% wt./wt.) | | | | | | |
|---|---|---|---|---|---|---|---|
| | 1 | 2 | 3 | 4 | 5 | 6 | 7 |
| Pendimethalin Tech. (91%) | 66.7 | 62.7 | 60.0 | 56.7 | 66.0 | 66.0 | 66.3 |
| Calcium Silicate | 5.0 | 4.7 | 4.5 | 4.2 | 5.0 | 5.0 | 5.0 |
| Sodium-N-Methyl-N-Oleoyltaurate | 2.5 | 2.4 | 2.2 | 2.1 | 2.5 | 2.5 | 2.5 |
| Sodium Naphthalene Formaldehyde Sulfonate, concensate | 5.0 | 9.7 | 9.5 | 9.2 | 5.0 | 5.0 | 5.0 |
| Bentonite Clay | 16.0 | 15.0 | 14.4 | 13.8 | 15.7 | 15.7 | — |
| Kaolin Clay | 4.3 | 4.0 | 4.0 | 3.6 | 4.3 | 4.3 | 20.7 |
| Sodium Tallowate | 0.5 | 0.5 | 0.4 | 0.4 | 0.5 | 0.5 | 0.5 |
| 2-Pyrrolidinone, 1-Ethenyl, Homopolymer | — | 1.0 | 5.0 | 10.0 | — | — | — |
| Sodium Hydroxide | — | — | — | — | 1.0 | — | — |
| Sodium Chloride | — | — | — | — | — | 1.0 | — |
| | 100% | 100% | 100% | 100% | 100% | 100% | 100% |

| Ingredient | (% wt./wt.) | | | | | | |
|---|---|---|---|---|---|---|---|
| | 8 | 9 | 10 | 11 | 12 | 13 | 14 |
| Pendimethalin Tech. (91%) | 54.1 | 59.2 | 62.7 | 54.1 | 55.5 | 63.4 | 58.2 |
| Imazaquin Tech. (97.5) | 8.9 | 9.0 | — | 8.9 | 9.1 | — | 9.2 |
| Imazethapyr (97.5%) | — | — | 4.5 | — | — | 4.0 | — |
| Calcium Silicate | 4.0 | 4.4 | 4.7 | 4.0 | 4.1 | 4.1 | 4.0 |
| Sodium-N-Methyl-N-Oleoyltaurate | — | 2.2 | 2.3 | — | — | — | — |
| Sodium Dioctyl Sulfosuccinate | — | — | — | 2.2 | — | — | — |
| Sodium Naphthalene Formaldehyde Sulfonate, condensate | 5.9 | 4.4 | 4.7 | 5.9 | — | 3.0 | 5.1 |
| Sodium Naphthalene Sulfonate/Alkyl Carboxylate blend | — | — | — | — | — | 1.0 | 3.2 |
| Bentonite Clay | 21.4 | 14.5 | 15.0 | 21.4 | 12.9 | 15.4 | 13.1 |
| Kaolin Clay | 3.5 | 3.7 | 4.0 | 3.5 | 3.6 | 4.1 | 3.7 |

-continued

| Ingredient | (% wt./wt.) | | | | | | |
|---|---|---|---|---|---|---|---|
| | 8 | 9 | 10 | 11 | 12 | 13 | 14 |
| Sodium Hydroxide | — | 2.6 | 2.1 | — | — | — | — |
| Potassim Phosphate (Tribasic) | — | — | — | — | 9.1 | — | 0.8 |
| Croscarmellose Sodium (internally crosslinked Sodium Carboxymethyl Cellulose) | — | — | — | — | 3.8 | 4.0 | 2.3 |
| Microcrystalline Cellulose | — | — | — | — | 1.9 | 1.0 | 0.8 |
| | 100% | 100% | 100% | 100% | 100% | 100% | 100% |

EXAMPLE 14

Evaluation of Dispersibility and Temperature Stability of the Test Compositions

Test compositions are stored at room temperature, 45° C. or 50° C. for 7 days, or up to 3 months, prior to evaluation. A predetermined amount of test composition, typically 1 gram or quantity sufficient to represent the maximum end use concentration, is added 100 mL of water in a graduated cylinder, which is then quickly stoppered. The cylinder is immediately rotated (inverted) 180°, and, after a 3 second pause, rotated an additional 180°, and held for 3 seconds. The cycle is then repeated. The number of 360° cycles required to completely dissolve/disperse the granules is recorded. The procedure is continued until 30 inversions have been made. The desired quick dispersion of the granules is reflected by the lower number of inversions (Table 1).

TABLE 1

| Dispersibility (# of Inversions) | | | |
|---|---|---|---|
| Example | 7 days @ RT | 7 days at 45° C. | 7 days @ 50° C. |
| 1 | 18 | 17 | 20 |
| 2 | 18 | 17 | 18 |
| 3 | 14 | 12 | 10 |
| 4 | 13 | 8 | 5 |
| 5 | 12 | 11 | 11 |
| 6 | 5 | 14 | 12 |
| 7 | 22 | 23 | 28 |
| | Initial @ RT | 3 months @ 45° C. | |
| 8 | 5 | >30 | |
| 9 | 6 | 14 | |
| 10 | 6 | 6 | |
| 11 | 5 | 24 | |
| 12 | 8 | 12 | |

EXAMPLE 15

Evaluation of Suspendibility of Test Composition

Test compositions are stored at room temperature, 45° C. or 50° C., for 7 days prior to evaluation. A predetermined amount of test composition is dispersed in a controlled aqueous system and allowed to settle for 30 minutes. An aliquot is taken from center of the suspension and the solids content is measured. The 30 minute reading is compared to, and reported as a percentage of, the presettling value. The desired suspendibility property of the composition is reflected by a higher percentage.

TABLE 2

| Suspendiblity (% Suspended) | | | |
|---|---|---|---|
| Example | 7 days @ RT | 7 days at 45° C. | 7 days @ 50° C. |
| 1 | 85.6 | 84.9 | 68.2 |
| 2 | 82.3 | 83.8 | 70.3 |

TABLE 2-continued

| Suspendiblity (% Suspended) | | | |
|---|---|---|---|
| Example | 7 days @ RT | 7 days at 45° C. | 7 days @ 50° C. |
| 3 | 79.2 | 83.0 | 68.6 |
| 4 | 79.7 | 78.2 | 64.7 |
| 5 | 82.2 | 83.5 | 68.8 |
| 6 | 29.6 | — | — |
| 7 | 86.9 | 22.2 | 17.8 |

As the results demonstrate, the WDG compositions of the invention possess improved dispersibility and suspendibility compared to the prior art formulations.

We claim:

1. A water dispersible granular composition comprising on a weight to weight basis about 20% to 90% of a dinitroaniline herbicide, in combination with about 1% to 20% of an imidazolinone herbicide; about 5% to 25% of a montmorillonite carrier; about 1.0% to 7.5% of a wetting agent; about 2% to 10% of a suspension agent; and about 0.5 to 20% of a dispersion enhancing agent.

2. The water dispersible granular composition according to claim 1 wherein the dispersion enhancing agent is selected from a base and a water swellable polymer.

3. The water dispersible granular composition according to claim 2 wherein the base is selected from an amine and an alkali metal hydroxide.

4. The water dispersible granular composition according to claim 3 wherein the base is selected from the group consisting of sodium hydroxide, potassium hydroxide and isopropyl amine.

5. The water dispersible granular composition according to claim 2 wherein the water swellable polymer comprises 2-pyrrolidinone, 1-ethenyl, homopolymer.

6. The water dispersible granular composition according to claim 2 wherein the water swellable polymer comprises cellulosic material.

7. The water dispersible granular composition according to claim 6 wherein the cellulosic material is selected from the group consisting of croscarmellose sodium and microcrystalline cellulose.

8. The water dispersible granular composition to claim 1, further comprising up to about 1% by weight of an antifoaming agent and up to about 7.5% by weight of a flow agent.

9. The water dispersible granular composition according to claim 1 wherein the dinitroaniline herbicide is selected from the group consisting of pendimethalin, trifluralin, isopropalin, ethalfluralin, benfluralin and oryzalin.

10. The water dispersible granular composition according to claim 1 wherein the imidazolinone herbicide is selected from imazaquin, imazethapyr, imazamethapyr and imazapyr.

11. The water dispersible granular composition according to claim 1 wherein the carrier is selected from the group consisting of beidellite, bentonite, nortronite, saponite, and mixtures thereof.

12. The water dispersible granular composition according to claim 11 wherein the carrier comprises bentonite.

13. A method for the production of a dinitroaniline-containing water dispersible granular composition having improved dispensability comprising the steps of:

(a) milling about 20% to 90% by weight of a dinitroaniline herbicides with about 1% to 20% by weight of an imidazolinone herbicide;

(b) blending the milled herbicide combination produced by step (a) with about 1% to 7.5% by weight of one or more wetting agents, about 2% to 10% by weight of one or more suspension agents and about 5% to 25% by weight of one or more montmorillonite carriers;

(c) milling the blend produced by step (b) in the presence of an unreactive refrigerant sufficient to cool the mill;

(d) mixing about 0.5% to 20% by weight of one or more dispersion enhancing agents with water and the milled blend produced by step (c);

(e) extruding the milled blend into granular compositions; and (f) drying the extruded granular compositions.

14. The method according to claim 13 wherein the dinitroaniline herbicide is selected from the group consisting of pendimethalin, trifluralin, isopropalin, ethalfluraline, benfluralin and oryzalin.

15. The method according to claim 13 wherein the imidazolinone herbicide is selected from the group consisting of imazaquin, imazethapyr, imazamethapyr and imazapyr.

16. The method according to claim 13 wherein step (b) further comprises the addition of up to about 1% by weight of one or more antifoaming agents and up to about 7.5% by weight of one or more flow agents.

17. The method according to claim 13 wherein the dispersion enhancing agent is selected from the group consisting of a base and a water swellable polymer.

18. The method according to claim 17 wherein the base is selected from the group consisting of amines and alkali metal hydroxides.

19. The method according to claim 17 wherein the water swellable polymer comprises 2-pyrrolidinone, 1-ethenyl-, homopolymer.

20. The method according to claim 17 wherein the water swellable polymer comprises a cellulosic material.

* * * * *